United States Patent [19]

Park et al.

[11] Patent Number: 5,354,886
[45] Date of Patent: Oct. 11, 1994

[54] CATALYSTS ON INORGANIC CARRIERS FOR PRODUCING ETHYLIDENE DIACETATE

[75] Inventors: Dae C. Park; Sung Y. Cho, both of Daejonjikhal, Rep. of Korea

[73] Assignee: Korea Research Institute of Chemical Technology, Daejonjikhal, Rep. of Korea

[21] Appl. No.: 97,647

[22] Filed: Jul. 26, 1993

Related U.S. Application Data

[62] Division of Ser. No. 772,257, Oct. 7, 1991, abandoned.

[30] Foreign Application Priority Data

Oct. 5, 1990 [KR] Rep. of Korea ............... 15829

[51] Int. Cl.$^5$ ............... B01J 31/20; B01J 31/24; B01J 31/18
[52] U.S. Cl. ............... 560/232; 562/598; 562/599
[58] Field of Search ............... 560/232; 562/598, 599, 562/519, 607, 406

[56] References Cited

U.S. PATENT DOCUMENTS

| | | | |
|---|---|---|---|
| 3,714,185 | 1/1973 | McCoy et al. | 260/326.5 FN |
| 3,855,307 | 12/1974 | Rony et al. | 260/604 HF |
| 3,940,043 | 12/1976 | Walker et al. | 260/449 R |
| 4,133,776 | 1/1979 | Pruett et al. | 252/431 N |
| 4,193,942 | 3/1980 | Gerritsen et al. | 260/604 HF |
| 4,246,183 | 1/1981 | Knifton | 260/408 |
| 4,302,547 | 11/1981 | Hart | 518/701 |
| 4,320,064 | 3/1982 | Vidal | 549/208 |
| 4,363,765 | 12/1982 | Fiato et al. | 549/208 |
| 4,405,821 | 9/1983 | Goetz | 568/862 |
| 4,434,247 | 2/1984 | Dombek | 518/700 |
| 4,690,912 | 9/1987 | Paulik et al. | 502/161 |

OTHER PUBLICATIONS

Rideal, Concepts in Catalysis, 1968, Pub. by Academic Press, N.Y., N.Y., pp. 4–5 (1968).

*Primary Examiner*—Arthur C. Prescott
*Attorney, Agent, or Firm*—Browning Bushman Anderson & Brookhart

[57] ABSTRACT

The present invention relates to a catalyst, a process for preparing the catalyst and a process for using the catalyst to produce ethylidene diacetate. The conventional preparation methods of ethylidene diacetate suffer from difficulty in separating the catalyst from the product after completion of the reaction. The catalyst of the present invention is simply separated from the product by mere filtration following the completion of reaction. This is a result of using a heterogenized catalyst which is obtained by supporting a homogeneous catalyst in an inorganic carder. The catalyst of the present invention is of the general formula $M_aX$ where M is a compound of a group VIII transition metal, most preferably $RhCl_3 \cdot xH_2O$, and X is an inorganic carrier, preferably selected from the group consisting of kieselguhr, $\gamma$-alumina, silica, $TiO_2$, MgO, ZnO and activated charcoal. Ethylidene diacetate produced using the present method is useful as an intermediate for producing precision chemical articles or as a starting material for the production of vinyl acetate monomer.

7 Claims, No Drawings

CATALYSTS ON INORGANIC CARRIERS FOR PRODUCING ETHYLIDENE DIACETATE

CROSS-REFERENCE TO RELATED APPLICATION

This application is a divisional application of application Ser. No. 07/772,257 filed Oct. 7, 1991, now abandoned.

BACKGROUND OF THE INVENTION

1. Field of the Invention

The present invention relates to catalysts on inorganic carriers useful for preparing ethylidene diacetate and to methods for preparing and using those catalysts in a continuous process for manufacturing ethylidene diacetate represented by the following formula:

$$CH_3CH(OCCH_3)_2 \quad (I)$$
(with a carbonyl O on the OCCH3 groups)

2. Background of the Invention

Various methods for producing ethylidene diacetate are known in the art. In all of these methods ethylidene diacetate has been prepared in batch reactor systems. Because known processes for preparing ethylidene diacetate employ a homogeneous catalytic reaction, there have been no known attempts to prepare this product by a continuous process. Conventional methods for preparing ethylidene diacetate have used homogeneous catalysts, e.g., transitional metals such as rhodium, ruthenium, palladium and platinum. Difficulties arose in separating these homogeneous catalysts from the reaction products.

There are few literature or patent references regarding methods for producing ethylidene diacetate. Several of these references disclose methods wherein methyl acetate, carbon monoxide and hydrogen are reacted in the presence of a homogeneous catalyst to produce ethylidene diacetate. While these methods which employ a homogeneous catalyst produce good selectivity and yield, all suffer from several significant disadvantages, including difficulties associated with separating and purifying the reaction products from the catalyst. Conventional homogeneous catalysts employed in these methods include complexes of group VIII transition metals, preferably rhodium, ruthenium, iridium, palladium and platinum. Japanese Patent No. 51-115409 and European Patent No. 0028474 disclose methods for producing ethylidene diacetate using a homogeneous rhodium catalyst. Japanese Patent No. 54-98713 and British Patent No. 1,112,555 disclose methods for producing ethylidene diacetate using homogeneous palladium catalysts. All of these methods suffer from difficulties in separating and purifying the reaction products from the homogeneous catalyst. These prior methods require the use of a distillation process to separate the homogeneous catalyst from the reaction products. For example, the '474 European patent, which discloses a method having a yield of 75.3% ethylidene diacetate based on dimethyl acetate starting material, requires a distillation step to separate the homogeneous catalyst from the reaction products.

The present invention solves the problems of the prior art by providing a novel catalyst system wherein the reaction products may be easily separated from a heterogeneous, supported catalyst. The catalyst and method of the present invention provide a simplified process for producing ethylirene diacetate and improve the productivity thereof while reducing the quantity of expensive, catalytic metal required.

By employing a catalyst supported on an inorganic carrier, the present invention solves the problems in the prior art caused by the difficulties in separating prior art homogeneous catalysts from the reaction products. The methods of the present invention simplify and improve the preparation and purification of ethylirene diacetate.

SUMMARY OF THE INVENTION

The present invention solves the problems of the prior art relating to the separation of homogeneous catalysts from reaction products by disclosing novel, heterogenous catalysts prepared by supporting homogeneous catalyst components on inorganic carriers. The use of these catalysts permits production methods employing low reaction temperatures and pressures, reduces the quantity of expensive metallic catalyst required and simplifies separation and purification of the reaction products.

The present invention is directed to a catalyst supported on an inorganic carrier useful for preparing ethylidene diacetate. The catalyst is represented by the following general formula:

$$M_aX \quad (II)$$

wherein M is a compound containing a group VIII transition metal and preferably selected from the group consisting of $RhCl_3 \cdot xH_2O$ and $RhCl(CO)[P(C_6H_5)_3]_2$;

X is an inorganic carrier preferably selected from the group consisting of kieselguhr, γ-alumina, activated charcoal, silica, titanium dioxide, magnesium oxide and zinc oxide; and a represents the weight percent of metal contained in the catalyst, preferably from about 0.1–2.0 weight percent.

The present invention further relates to a process for preparing the catalyst of formula (II) by adding compound M and carrier X, both as defined as above, to distilled water, heating the resulting mixture to a temperature between about 50–100° C., precipitating, filtering and drying at a temperature of about 90–150° C. to produce the catalyst of formula (II).

Finally, the present invention also relates to a process for preparing ethylidene diacetate using the novel, supported catalyst by reacting methyl acetate, iodomethane, carbon monoxide and hydrogen in the presence of the catalyst of formula (II) and an accelerator at a temperature between about 90–250° C. and at a pressure between about 20–70 atmospheres.

Using the foregoing heterogenous catalyst, separation and purification of the catalyst from the ethylidene diacetate produced in the reaction is easily accomplished by a simple filtration process. Thus, complex separation steps, including distillation, required in prior methods using homogeneous catalysts are eliminated. Accordingly, use of the foregoing heterogenous catalyst solves the prior art difficulties and simplifies the processes necessary for separating and purifying the produced ethylirene diacetate.

DETAILED DESCRIPTION OF THE INVENTION

In the processes of the present invention, using a heterogeneous catalyst comprising a group VIII transition metal compound supported on an inorganic carrier, ethylidene diacetate was produced with a yield as great as 40.8% based on methyl acetate by using a catalyst comprising $RhCl_3 \cdot xH_2O/\gamma$-alumina and containing 0.56 weight percent rhodium based on the catalyst weight. Further, the catalyst was easily separated from the reaction products by simple filtration. Thus, the complicated conventional separation processes required to separate and recover produced ethylidene diacetate from conventional homogeneous catalysts are unnecessary and the manufacturing process is greatly simplified by using the heterogeneous catalyst of formula (II). Because of the simplification of the reaction process by the elimination of distillation and other separation and purification steps, the reaction apparatus also is similarly simplified.

The catalyst of formula (II) is prepared on an inorganic carrier by first drying the carrier in a vacuum desiccator. About 0.10–0.90 mmole of metal compound M and about 2–4 grams of an inorganic carrier are added to about 20–40 ml of distilled water. The resulting mixture is maintained at a temperature of 85–100° C. The crude catalyst is precipitated from this mixture. The precipitated catalyst is dried, e.g., it is separated by filtration and dried at a temperature of about 120–150° C.

The metal compound M is a compound of a group VIII transition metal, preferably rhodium, and most preferably is selected from the group consisting of $RhCl_3 \cdot xH_2O$ and $RhCl(CO)[P(C_6H_5)_3]_2$. The inorganic carrier X is selected from the group consisting of kieselguhr, $\gamma$-alumina, activated charcoal, silica, titanium dioxide, magnesium oxide and zinc oxide. The presently most preferred inorganic carriers are selected from the group consisting of kieselguhr, $\gamma$-alumina and silica.

Ethylidene diacetate is produced by reacting hydrogen, carbon monoxide, methyl acetate and iodomethane in the presence of the supported, heterogeneous catalyst of formula (II). When using a catalyst of formula (II) in the process of producing ethylidene diacetate, it is preferable to include in the process an organic accelerator. The most preferred organic accelerator is 3-picoline. It has been found that inorganic accelerators do not increase the yield of ethylidene diacetate.

In the methods for producing ethylidene diacetate using the catalyst of formula (II) the following reaction conditions should be maintained. The molar ratio of hydrogen to carbon monoxide feed should be from about 1:1 to about 6:1, more preferably from about 1:1 to about 3:1. The reaction temperature should be maintained between about 100–200° C., most preferably between about 130–180° C. The concentration of catalyst should be between about 0.1–5.0 weight percent of total reactants, more preferably between about 0.1–2.5 weight percent of total reactants and most preferably between about 0.2–1.5 weight percent based on total reactants. The concentration of iodomethane should be maintained between about 10–99 weight percent of total reactants, preferably between about 20–60 weight percent of total reactants. The reaction pressure should be maintained between about 10–90 atmospheres, preferably between about 20–80 atmospheres.

The yield, conversion and selectivity of the process of this invention are defined according to the following equations.

$$\text{Yield(mole \%)} = \frac{\text{(moles of ethylidene diacetate produced)}}{\text{(moles of methyl acetate feed)}} \times 100\%$$

$$\text{Conversion(mole \%)} = \frac{\text{(moles of methyl acetate reacted)}}{\text{(moles of methyl acetate feed)}} \times 100\%$$

$$\text{Selectivity(mole \%)} = \frac{\text{(moles of ethylidene diacetate produced)}}{\text{(moles of methyl acetate reacted)}} \times 100\%$$

The starting materials and products were quantitatively analyzed using gas chromatography from correlation curves obtained using anisole as the standard material to reactants and products.

The present invention will be illustrated in more detail by the following examples.

PREPARATION OF THE CATALYST

The following examples 1–7 illustrate preparation of catalysts in accord with the present invention.

EXAMPLE 1

$\gamma$-alumina was dried at 150° C. for 24 hours in a vacuum desiccator. 3.3 g of the dried $\gamma$-alumina and 0.150 g (0.176 mmole) of $RhCl_3 \cdot xH_2O$ were added to 20 ml of distilled water. After the precipitate had completely formed, the moisture was evaporated by maintaining the temperature at 90° C. The precipitate was dried at 120° C. to produce a catalyst of $RhCl_3 \cdot xH_2O/\gamma$-alumina containing 1.8 weight percent rhodium based on total catalyst weight.

EXAMPLE 2

The procedure of Example 1 was repeated except that the precipitating temperature was changed to 25° C. A catalyst having the same formula and rhodium content was produced.

EXAMPLE 3

The procedure of Example 1 was repeated except that the reactants were 0.102 g (0.483 mmole) of $RhCl_3 \cdot xH_2O$ and 4.0 g of $SiO_2$. A catalyst of $RhCl_3 \cdot xH_2O/SiO_2$ containing 1.4 weight percent rhodium based on total catalyst weight was produced.

EXAMPLE 4

The procedure of Example 1 was repeated except that the reactants were 0.120 g (0.574 mmole) of $RhCl_3 \cdot xH_2O$ and 3.16 g of ZnO. A catalyst of $RhCl_3 \cdot xH_2O/$ ZnO containing 1.6 weight percent rhodium based on total catalyst weight was produced.

EXAMPLE 5

The procedure of Example 1 was repeated except that the reactants were 0.16 g (0.668 mmole) of $RhCl_3 \cdot xH_2O$ and 3.12 g of MgO. A catalyst of $RhCl_3 \cdot xH_2O/MgO$ containing 1.9 weight percent rhodium based on total catalyst weight was produced.

EXAMPLE 6

The procedure of Example 1 was repeated except that the reactants were 0.160 g (0.765 mmole) of $RhCl_3 \cdot xH_2O$ and 3.27 g of activated charcoal. A catalyst of $RhCl_3 \cdot xH_2O/$activated charcoal containing 2.0 weight percent rhodium based on total catalyst weight was produced.

EXAMPLE 7

The procedure of Example 1 was repeated except that the reactants were 0.180 g (0.860 mmole) of $RhCl_3 \cdot xH_2O$ and 3.80 g of $TiO_2$. A catalyst of $RhCl_3 \cdot xH_2O/TiO_2$ containing 2.3 weight percent rhodium based on total catalyst weight was produced.

PREPARATION OF ETHYLIDENE DIACETATE

The following examples 8–17 illustrate the preparation of ethylidene diacetate using catalysts prepared in accord with the present invention.

EXAMPLE 8

A stainless steel autoclave having an internal capacity of 70 ml and operated at an internal pressure of 150 kg/cm² was used. The reactor was purged with nitrogen to eliminate air. The reactor was charged with 31.0 g (0.4184 mmole) of methyl acetate, 12.2 g (83 mmole) of iodomethane, 2,8 g ((0.56 mmole) of a catalyst having the formula $RhCl_3 \cdot xH_2O/\gamma$-alumina (0.56 wt. % Rh), 2.01 g (20.1 mmole) of 3- picoline as an accelerator, hydrogen and carbon monoxide. The resulting mixture was reacted with stirring at 150° C. and 70 atmospheres pressure for 4 hours and then cooled to room temperature. The mixture was filtered to separate the precipitated product from the catalyst and the reaction products were analyzed by gas chromatography.

The results of the gas chromatographic analysis are shown in Table 1.

TABLE 1

| Rh (wt %) | Amount of catalyst g | mmole | Reaction time (hr) | Based on methyl acetate Conversion (%) | Yield (%) | Conversion (%) |
|---|---|---|---|---|---|---|
| 0.56 | 2.8 | 0.56 | 4 | 98.7 | 40.8 | 99.0 |

| | Yield (%) | | | Selectivity (%) | |
|---|---|---|---|---|---|
| ED* | Anhydrous acetic acid | Acetic acid | ED* | Anhydrous acetic acid | Acetic acid |
| 32.3 | 0 | 67.4 | 32.6 | 0 | 67.4 |

*Ed: Ethylidene diacetate

EXAMPLE 9

The procedure of Example 8 was repeated except that the reactants were 20.1 g (257.6 mmole) of methyl acetate, 7.13 g (48.7 mmole) of iodomethane, 4.05 g (0.19 mmole) of $RhCl_3 \cdot xH_2O/\gamma$-alumina (0.5 wt. % Rh) catalyst and 1.23 g (13.0 mmole) of 3-picoline accelerator.

The results of the gas chromatographic analysis of the precipitated and dried reaction products are shown in Table 2.

TABLE 2

| Rh (wt %) | Amount of catalyst g | mmole | Reaction time (hr) | Based on methyl acetate Conversion (%) | Yield (%) | Conversion (%) |
|---|---|---|---|---|---|---|
| 0.50 | 4.0 | 0.19 | 4 | 50.3 | 11.6 | 55.2 |

| | Yield (%) | | | Selectivity (%) | |
|---|---|---|---|---|---|
| ED* | Anhydrous acetic acid | Acetic acid | ED* | Anhydrous acetic acid | Acetic acid |
| 10.5 | 16.1 | 28.6 | 19.0 | 29.1 | 51.9 |

*Ed: Ethylidene diacetate

EXAMPLE 10

The procedure of Example 8 was repeated except that the reaction time was varied and the catalyst used was 4.4 g (0.67 mmole) of $RhCl_3 \cdot xH_2O/SiO_2$ (1.40wt. % Rh).

The results of the gas chromatographic analysis of reaction products are shown in Table 3.

TABLE 3

| Rh (wt %) | Amount of catalyst g | mmole | Reaction time (hr) | Based on methyl acetate Conversion (%) | Yield (%) | Conversion (%) |
|---|---|---|---|---|---|---|
| 1.40 | 4.4 | 0.67 | 1 | 40.8 | 7.5 | 40.4 |
| | | | 1.5 | 41.6 | 13.1 | 39.7 |
| | | | 2 | 50.2 | 14.1 | 57.1 |
| | | | 2.5 | 60.8 | 22.4 | 65.9 |
| | | | 3 | 62.5 | 27.7 | 70.4 |
| | | | 3.5 | 63.01 | 24.7 | 67.8 |
| | | | 4 | 67.0 | 28.3 | 67.7 |

| | Yield (%) | | | Selectivity (%) | |
|---|---|---|---|---|---|
| ED* | Anhydrous acetic acid | Acetic acid | ED* | Anhydrous acetic acid | Acetic acid |
| 7.6 | 7.4 | 25.4 | 18.9 | 18.2 | 62.9 |
| 13.5 | 13.5 | 26.2 | 34.0 | 0 | 66.0 |
| 12.2 | 12.2 | 37.6 | 21.4 | 12.7 | 65.9 |
| 21.5 | 21.5 | 37.7 | 29.5 | 14.9 | 55.6 |
| 21.8 | 21.8 | 38.1 | 31.0 | 14.9 | 54.1 |
| 21.4 | 21.4 | 36.8 | 31.6 | 14.2 | 54.2 |
| 25.7 | 25.7 | 41.9 | 38.1 | 0 | 61.9 |

*Ed: Ethylidene diacetate

EXAMPLE 11

The procedure of Example 8 was repeated except that the reaction time was varied and the catalyst used was 3.3 g (0.72 mmole) of $RhCl_3 \cdot xH_2O/\gamma$-alumina (1.80 wt. % Rh).

The results of the gas chromatographic analysis of reaction products are shown in Table 4.

TABLE 4

| Rh (wt %) | Amount of catalyst g | mmole | Reaction time (hr) | Based on methyl acetate Conversion (%) | Yield (%) | Conversion (%) |
|---|---|---|---|---|---|---|
| 1.80 | 3.3 | 0.72 | 1 | 39.9 | 10.8 | 36.8 |
| | | | 1.5 | 51.5 | 10.8 | 45.9 |
| | | | 2 | 56.8 | 13.2 | 53.2 |
| | | | 2.5 | 62.0 | 15.3 | 58.1 |
| | | | 3 | 64.2 | 17.1 | 56.9 |
| | | | 3.5 | 64.5 | 15.2 | 62.2 |
| | | | 4 | 62.3 | 18.1 | 62.5 |

| | Yield (%) | | | Selectivity (%) | |
|---|---|---|---|---|---|
| ED* | Anhydrous acetic acid | Acetic acid | ED* | Anhydrous acetic acid | Acetic acid |
| 11.3 | 8.2 | 17.2 | 30.8 | 22.4 | 46.8 |
| 12.2 | 5.2 | 28.7 | 26.2 | 11.3 | 62.5 |
| 14.4 | 5.9 | 32.9 | 27.0 | 11.0 | 62.0 |
| 16.9 | 6.5 | 34.6 | 29.2 | 11.2 | 59.6 |
| 22.4 | 10.2 | 24.3 | 39.3 | 18.0 | 42.7 |
| 16.2 | 8.2 | 37.8 | 26.0 | 13.5 | 60.8 |
| 18.0 | 6.6 | 37.9 | 28.8 | 10.5 | 60.7 |

*Ed: Ethylidene diacetate

EXAMPLE 12

The procedure of Example 8 was repeated except that the reaction time was varied and the catalyst used was 3.2 g (0.72 mmole) of $RhCl_3 \cdot xH_2O$/activated charcoal (2.01 wt. % Rh).

The results of the gas chromatographic analysis of reaction products are shown in Table 5.

TABLE 5

| Rh (wt %) | Amount of catalyst g | mmole | Reaction time (hr) | Based on methyl acetate Conversion (%) | Yield (%) | Conversion (%) |
|---|---|---|---|---|---|---|
| 2.01 | 3.3 | 0.72 | 0.5 | 0 | 0 | 0 |
| | | | 1.5 | 3.8 | 0.6 | 10.6 |
| | | | 2.75 | 9.6 | 6.6 | 19.5 |
| | | | 3.25 | 42.1 | 9.9 | 27.7 |
| | | | 3.75 | 54.6 | 12.6 | 34.9 |
| | | | 4.5 | 58.3 | 21.6 | 51.9 |
| | | | 5 | 66.5 | 32.7 | 67.6 |

| Yield (%) | | Selectivity (%) | | |
|---|---|---|---|---|
| ED* | Anhydrous acetic acid | Acetic acid | ED* | Anhydrous acetic acid | Acetic acid |
| 0 | 0 | 0 | 0 | 0 | 0 |
| 0.5 | 10.1 | 0 | 4.8 | 95.2 | 0 |
| 5.8 | 13.7 | 0 | 29.8 | 70.2 | 0 |
| 12.5 | 15.2 | 0 | 45.0 | 55.0 | 0 |
| 18.1 | 16.8 | 0 | 51.9 | 48.1 | 0 |
| 24.9 | 7.6 | 19.4 | 47.9 | 14.8 | 37.5 |
| 31.6 | 16.8 | 19.2 | 46.7 | 24.8 | 28.5 |

*Ed: Ethylidene diacetate

EXAMPLE 13

The procedure of Example 8 was repeated except that the reaction time was varied and the catalyst used was 3.17 g (0.73 mmole) of $RhCl_3 \cdot xH_2O$/γ-alumina (2.06 wt. % Rh).

The results of the gas chromatographic analysis of reaction products are shown in Table 6.

TABLE 6

| Rh (wt %) | Amount of catalyst g | mmole | Reaction time (hr) | Based on methyl acetate Conversion (%) | Yield (%) | Conversion (%) |
|---|---|---|---|---|---|---|
| 2.06 | 3.2 | 0.73 | 1 | 26.8 | 10.8 | 32.8 |
| | | | 1.5 | 42.3 | 19.8 | 46.5 |
| | | | 2 | 56.8 | 26.4 | 59.8 |
| | | | 2.5 | 56.8 | 27.9 | 61.7 |
| | | | 3 | 66.5 | 29.5 | 68.5 |
| | | | 3.5 | 69.8 | 33.1 | 73.4 |
| | | | 4 | 79.2 | 39.1 | 82.6 |

| Yield (%) | | | Selectivity (%) | | |
|---|---|---|---|---|---|
| ED* | Anhydrous acetic acid | Acetic acid | ED* | Anhydrous acetic acid | Acetic acid |
| 9.9 | 8.4 | 14.2 | 30.3 | 25.6 | 44.1 |
| 18.4 | 10.9 | 17.6 | 39.6 | 23.4 | 37.0 |
| 24.6 | 11.3 | 23.9 | 41.1 | 19.0 | 39.9 |
| 24.7 | 11.9 | 25.1 | 40.0 | 19.3 | 40.7 |
| 27.7 | 12.4 | 28.4 | 40.4 | 18.1 | 41.5 |
| 29.0 | 12.7 | 31.1 | 39.5 | 17.3 | 43.2 |
| 32.8 | 14.0 | 35.7 | 39.7 | 17.0 | 43.3 |

*Ed: Ethylidene diacetate

EXAMPLE 14

The procedure of Example 8 was repeated except that the reaction time was varied and the catalyst used was 3.80 g (0.9 mmole) of $RhCl_3 \cdot xH_2O$/$TiO_2$ (2.30 wt. % Rh).

The results of the gas chromatographic analysis of reaction products are shown in Table 7.

TABLE 7

| Rh (wt %) | Amount of catalyst g | mmole | Reaction time (hr) | Based on methyl acetate Conversion (%) | Yield (%) | Conversion (%) |
|---|---|---|---|---|---|---|
| 2.30 | 3.8 | 0.9 | 1 | 40.9 | 4.7 | 21.9 |
| | | | 1.5 | 46.3 | 8.7 | 24.1 |
| | | | 2 | 51.7 | 15.1 | 39.5 |
| | | | 2.5 | 58.6 | 21.2 | 51.1 |
| | | | 3 | 66.7 | 21.4 | 58.1 |
| | | | 3.5 | 70.4 | 26.2 | 64.5 |
| | | | 4 | 70.8 | 29.2 | 70.8 |

| Yield (%) | | | Selectivity (%) | | |
|---|---|---|---|---|---|
| ED* | Anhydrous acetic acid | Acetic acid | ED* | Anhydrous acetic acid | Acetic acid |
| 6.2 | 0 | 15.7 | 28.2 | 0 | 71.8 |
| 12.4 | 0 | 11.7 | 51.5 | 0 | 48.5 |
| 18.8 | 5.5 | 15.2 | 47.7 | 13.9 | 38.4 |
| 25.1 | 9.1 | 16.9 | 49.1 | 17.8 | 33.1 |
| 26.9 | 9.1 | 22.0 | 46.4 | 15.7 | 37.9 |
| 31.4 | 8.4 | 24.7 | 48.7 | 13.0 | 38.3 |
| 29.2 | 11.7 | 29.9 | 41.2 | 16.5 | 42.3 |

*Ed: Ethylidene diacetate

EXAMPLE 15

The procedure of Example 8 was repeated except that the reaction time was varied and the catalyst used was 3.27 g (0.2 mmole) of $RhCl(CO)[P(C_6H_5)_3]_2$/γ-alumina (0.30 wt. % Rh).

The results of the gas chromatographic analysis of reaction products are shown in Table 8.

TABLE 8

| Rh (wt %) | Amount of catalyst g | mmole | Reaction time (hr) | Based on methyl acetate Conversion (%) | Yield (%) | Conversion (%) |
|---|---|---|---|---|---|---|
| 0.30 | 3.2 | 0.2 | 1 | 31.0 | 10.9 | 24.8 |
| | | | 1.5 | 38.1 | 18.4 | 36.3 |
| | | | 2 | 47.9 | 24.5 | 47.5 |
| | | | 2.5 | 60.9 | 30.6 | 60.0 |
| | | | 3 | 63.8 | 33.9 | 62.9 |
| | | | 3.5 | 69.2 | 36.7 | 69.6 |
| | | | 4 | 70.8 | 40.0 | 72.5 |

| Yield (%) | | | Selectivity (%) | | |
|---|---|---|---|---|---|
| ED* | Anhydrous acetic acid | Acetic acid | ED* | Anhydrous acetic acid | Acetic acid |
| 11.9 | 12.8 | 0 | 48.2 | 51.8 | 0 |
| 18.8 | 7.5 | 9.9 | 51.9 | 20.7 | 27.4 |
| 24.7 | 9.9 | 12.8 | 52.0 | 21.0 | 26.9 |
| 31.3 | 7.7 | 20.9 | 52.2 | 12.9 | 34.9 |
| 34.6 | 4.8 | 23.6 | 54.9 | 7.6 | 37.5 |
| 36.2 | 7.6 | 25.8 | 52.0 | 11.0 | 37.0 |
| 37.7 | 6.4 | 28.4 | 51.9 | 8.9 | 39.2 |

*Ed: Ethylidene diacetate

EXAMPLE 16

The procedure of Example 8 was repeated except that the catalyst used was 3.16 g (0.6 mmole) of $RhCl_3 \cdot xH_2O$/ZnO (1.60 wt. % Rh).

The results of the gas chromatographic analysis of reaction products are shown in Table 9.

TABLE 9

| Rh (wt %) | Amount of catalyst g | mmole | Reaction time (hr) | Based on methyl acetate Conversion (%) | Yield (%) | Conversion (%) |
|---|---|---|---|---|---|---|

TABLE 9-continued

| | | | | | | |
|---|---|---|---|---|---|---|
| 1.60 | 3.2 | 0.6 | 4 | 49.2 | 0 | 37.3 |

| Yield (%) | | | Selectivity (%) | | |
|---|---|---|---|---|---|
| ED* | Anhydrous acetic acid | Acetic acid | ED* | Anhydrous acetic acid | Acetic acid |
| 0 | 9.1 | 19.2 | 0 | 32.2 | 67.8 |

*Ed: Ethylidene diacetate

EXAMPLE 17

The procedure of Example 8 was repeated except that the catalyst used was 3.12 g (0.7 mmole) of $RhCl_3 \cdot xH_2O/MgO$ (1.91 wt. % Rh).

The results of the gas chromatographic analysis of reaction products are shown in Table 10.

TABLE 10

| Rh (wt %) | Amount of catalyst | | Reaction time (hr) | Based on methyl acetate | | Conversion (%) |
|---|---|---|---|---|---|---|
| | g | mmole | | Conversion (%) | Yield (%) | |
| 1.92 | 3.1 | 0.7 | 4 | 63.9 | 0 | 53.5 |

| Yield (%) | | | Selectivity (%) | | |
|---|---|---|---|---|---|
| ED* | Anhydrous acetic acid | Acetic acid | ED* | Anhydrous acetic acid | Acetic acid |
| 0 | 0 | 53.5 | 0 | 0 | 100 |

*Ed: Ethylidene diacetate

As shown in the results illustrated in Tables 1 to 10, the process of the present invention for producing ethylidene diacetate using a catalyst produced in accord with the present invention has several advantages. No by-product is formed except acetic acid. The purification of ethylidene diacetate is simplified because the catalyst is not mixed with the reaction product. Energy and time required for the process is reduced because complex separation procedures are not required. The process is simplified since no distillation step is required for purification of the product.

The foregoing description of the invention has been directed in primary part to a particular preferred embodiment and method in accordance with the requirements of the patent statutes and for purposes of explanation and illustration. It will be apparent, however, to those skilled in the art that many modifications and changes in the specifically described catalysts and methods may be made without departing from the scope and spirit of the invention. Therefore, the invention is not restricted to the particular catalysts and methods illustrated and described, but covers all modifications which may fall within the scope of the following claims.

It is Applicants' intention in the following claims to cover such modifications and variations as fall within the true spirit and scope of the invention.

What is claimed is:

1. A process for preparing ethylidene diacetate comprising reacting at a temperature between about 90–250° C. and at a pressure between about 20–70 atmospheres, methyl acetate, iodomethane, carbon monoxide and hydrogen in the presence of an accelerator and a supported catalyst represented by the formula $M_aX$ wherein, M is a compound of a group VIII transition metal which catalyzes the production of ethylidene diacetate;

X is an inorganic carrier; and a represents the weight percent of said metal in said catalyst.

2. The process of claim 1 wherein said compound M is selected from the group consisting of $RhCl_3 \cdot xH_2O$ and $RhCl(CO)[P(C_6H_5)_3]_2$.

3. The process of claim 2 wherein said carrier X is selected from the group consisting of kieselguhr, γ-alumina, silica, activated charcoal, $TiO_2$, MgO and ZnO.

4. The process of claim 3 wherein said weight percent of said metal is from about 0.1–2.0 weight percent.

5. The process of claim 4 wherein said accelerator is 3-picoline.

6. The process of claim 1 wherein the molar ratio of hydrogen to carbon monoxide is between about 1:1 and about 6:1.

7. The process of claim 1 wherein said catalyst comprises about 0.1–5.0 weight percent of total reactants, said iodomethane comprises about 20–70 weight percent of total reactants and said accelerator comprises about 1–10 weight percent of total reactants.

* * * * *